(12) United States Patent
Kramer

(10) Patent No.: US 10,064,408 B2
(45) Date of Patent: Sep. 4, 2018

(54) BIRD REPELLING TREATMENT COMPOSITION

(75) Inventor: Daniel R. Kramer, Huntington Woods, MI (US)

(73) Assignee: AVIAN ENTERPRISES, LLC, St. Petersburg, FL (US)

( * ) Notice: Subject to any disclaimer, the term of this patent is extended or adjusted under 35 U.S.C. 154(b) by 1238 days.

(21) Appl. No.: 12/473,853

(22) Filed: May 28, 2009

(65) Prior Publication Data

US 2010/0303751 A1   Dec. 2, 2010

(51) Int. Cl.
*A01N 37/44* (2006.01)
*A01N 37/10* (2006.01)
*A61L 9/01* (2006.01)
*A61L 9/14* (2006.01)

(52) U.S. Cl.
CPC ............ *A01N 37/44* (2013.01); *A01N 37/10* (2013.01); *A61L 9/01* (2013.01); *A61L 9/14* (2013.01); *A61L 2209/21* (2013.01)

(58) Field of Classification Search
CPC  A01N 37/44; A01N 37/10; A61L 9/01; A61L 9/14; A61L 2209/21
USPC .................................. 424/76.8, 400; 514/537
See application file for complete search history.

(56) References Cited

U.S. PATENT DOCUMENTS

| | | | |
|---|---|---|---|
| 2,967,128 A * | 1/1961 | Kare | 514/535 |
| 6,159,262 A * | 12/2000 | Tumbers | C05F 3/00 71/11 |
| 6,192,621 B1 | 2/2001 | Fain | |
| 9,526,242 B2 * | 12/2016 | Black | A01N 37/44 |
| 2006/0034898 A1 * | 2/2006 | Amodt | A01N 25/34 424/443 |
| 2006/0251691 A1 | 11/2006 | Crawford | |

FOREIGN PATENT DOCUMENTS

| | | | |
|---|---|---|---|
| DE | 10 2004 042695 A1 | 3/2006 | |
| EP | 1 897 565 A1 | 3/2008 | |
| EP | 1897565 A1 * | 3/2008 | A61L 9/01 |
| JP | 2003-261895 A | 9/2003 | |

OTHER PUBLICATIONS

Scotts Miracle Gro® [Downloaded Jul. 11, 2011] [Retrieved from internet <URLs: http://www.scotts.com/smg/catalog/productCategoryLanding.jsp?itemId=cat50010&navAction=jump ; http://www.scotts.com/smg/catalog/productCategorySubSelf.jsp?itemId=cat50106&navAction=jump ; http://www.scotts.com/smg/catalog/productTemplate.jsp?proId=prod140002&itemId=cat50148 >], 4 pages.*
Herb-Magic.com (Gum Arabic Resin [Downloaded Dec. 30, 2011] [Retrieved from internet <URL: http://herb-magic.com/gum-arabic.html >]), 3 pages.*
Mason et al., Evaluation of Methyl Anthranilate and Starch-Plated Dimethyl Anthranilate as Bird Repellent Feed Additives, J. Wildl. Manage., 55(1): 182-187 (1991), 6 pages.*
Avery et al. (Mint plant derivatives as blackbird feeding deterrents, Crop Protection (1996) 15 (5): 461-464), 4 pages.*
Mason et al. (Evaluation of Methyl Anthranilate and Starch-Plated Dimethyl Anthranilate as Bird Repellent Feed Additives, J. Wildlife Manage. (1991) 55 (1): 182-187), 6 pages.*
PubChem, Methyl 2-(methylamino)benzoate, [Retrieved from internet <URL: http://pubchem.ncbi.nlm.nih.gov/compound/Methyl_2-_ methylamino_benzoate >] [Downloaded May 13, 2015], 19 pages.*
Brunning, The Chemistry of the Odour of Decomposition, Compound Interest, [Retrieved from internet <URL: http://www.compoundchem.com/2014/10/30/decompositionodour/ >], (Oct. 30, 2014), 10 pages.*
Kabara et al., Fatty Acids and Derivatives as Antimicrobial Agents, Antimicrobial Agents and Chemotherapy (1972), vol. 2, No. 1, pp. 23-28 (Year: 1972).*
EP Extended Search Report, dated Jul. 28, 2010, 2 pgs.
Aerosol Definition, merriam-webster.com, accessed Jul. 23, 2013 (2 pgs.).
Atomize Definition, merriam-webster.com, accessed Jul. 23, 2013 (2 pgs.).
"How Aerosol Cans Work" (http://science.howstuffworks.com/innovation/everyday-innovations/aerosol-can3.htm/printable), accessed Jul. 29, 2013 (2 pgs.).
EWG—"Geraniol" (http://www.ewg.org/skindeep/ingredient/702568/GERANIOL/) accessed Mar. 28, 2014 (2 pgs.).

* cited by examiner

*Primary Examiner* — Brian-Yong S Kwon
*Assistant Examiner* — Miriam A Levin
(74) *Attorney, Agent, or Firm* — Brooks Kushman P.C.

(57) ABSTRACT

A concentrated treatment composition includes a bird repelling composition, a glycol, and a fragrance-containing/odor control composition. The concentrated treatment composition provides a stable product that is miscible with water. Methods for applying to the treatment compositions are also provided.

2 Claims, No Drawings

US 10,064,408 B2

BIRD REPELLING TREATMENT COMPOSITION

BACKGROUND OF THE INVENTION

1. Field of the Invention

In at least one aspect, the present invention relates to compositions for relieving one or more unpleasant characteristics of a location that tends to attract birds.

2. Background Art

Landfills present a number of undesirable characteristics that require improvement. The odor emitted from landfills is particularly troubling for nearby residential communities. Another unattractive feature is the tendency for landfills to attract large numbers of birds with potential associated aesthetic and health concerns. Other facilities are also known to undesirably attract birds. Examples of such facilities include golf courses, airports, sporting arenas, areas with standing water, waste water treatment plants, athletic fields, retention ponds, lagoons, and compost facilities.

Compositions and methodologies exist for both odor and bird control. Currently, odor control compositions are applied separately from the application of bird control compositions. Obviously, each composition is applied at a separate time usually by a different crew.

Accordingly, there is a need for improved compositions and methods for improving both odor and bird control.

SUMMARY OF THE INVENTION

The present invention solves one or more problems of the prior art by providing in at least one embodiment a concentrated treatment composition for odor and/or bird control. The concentrated treatment composition is useful for treating environments (e.g., landfills, golf courses, airports, sporting arenas, areas with standing water, waste water treatment plants, athletic fields, retention ponds, lagoons, and compost facilities) that emit unpleasant odors and attract an undesirably large number of birds. The composition of this embodiment includes a bird repelling composition and a glycol. Advantageously, the compositions of this embodiment are substantially free of surfactants. Moreover, the concentrated treatment composition provides a stable product that is miscible in water.

In another embodiment, a concentrated treatment composition for odor and/or bird control is provided. The concentrated treatment composition is useful for treating environments (e.g., landfills, golf courses, airports, sporting arenas, areas with standing water, waste water treatment plants, athletic fields, retention ponds, lagoons, and compost facilities) that emit unpleasant odors and attract an undesirably large number of birds. The composition of this embodiment includes a bird repelling composition, a glycol, and a fragrance-containing/odor control composition. Advantageously, the compositions of this embodiment are substantially free of surfactants. Moreover, the concentrated treatment composition provides a stable product that is miscible with water.

In another embodiment of the present invention, a diluted treatment composition for odor and bird control is provided. The compositions of the present embodiment correspond to dilutions of the concentrated compositions set forth above.

In still other embodiments, methods of applying the compositions set forth above are provided.

DETAILED DESCRIPTION OF THE PREFERRED EMBODIMENT(S)

Reference will now be made in detail to presently preferred compositions, embodiments and methods of the present invention, which constitute the best modes of practicing the invention presently known to the inventors. The Figures are not necessarily to scale. However, it is to be understood that the disclosed embodiments are merely exemplary of the invention that may be embodied in various and alternative forms. Therefore, specific details disclosed herein are not to be interpreted as limiting, but merely as a representative basis for any aspect of the invention and/or as a representative basis for teaching one skilled in the art to variously employ the present invention.

Except in the examples, or where otherwise expressly indicated, all numerical quantities in this description indicating amounts of material or conditions of reaction and/or use are to be understood as modified by the word "about" in describing the broadest scope of the invention. Practice within the numerical limits stated is generally preferred. Also, unless expressly stated to the contrary: percent, "parts of," and ratio values are by weight; the description of a group or class of materials as suitable or preferred for a given purpose in connection with the invention implies that mixtures of any two or more of the members of the group or class are equally suitable or preferred; description of constituents in chemical terms refers to the constituents at the time of addition to any combination specified in the description, and does not necessarily preclude chemical interactions among the constituents of a mixture once mixed; the first definition of an acronym or other abbreviation applies to all subsequent uses herein of the same abbreviation and applies mutatis mutandis to normal grammatical variations of the initially defined abbreviation; and, unless expressly stated to the contrary, measurement of a property is determined by the same technique as previously or later referenced for the same property.

It is also to be understood that this invention is not limited to the specific embodiments and methods described below, as specific components and/or conditions may, of course, vary. Furthermore, the terminology used herein is used only for the purpose of describing particular embodiments of the present invention and is not intended to be limiting in any way.

It must also be noted that, as used in the specification and the appended claims, the singular form "a," "an," and "the" comprise plural referents unless the context clearly indicates otherwise. For example, reference to a component in the singular is intended to comprise a plurality of components.

Throughout this application, where publications are referenced, the disclosures of these publications in their entireties are hereby incorporated by reference into this application to more fully describe the state of the art to which this invention pertains.

The following description of the embodiment(s) is merely exemplary in nature and is in no way intended to limit the invention, its application, or uses.

In an embodiment of the present invention, a concentrated treatment composition that is useful for treating environments (e.g., landfills, golf courses, airports, sporting arenas, areas with standing water, waste water treatment plants, athletic fields, retention ponds, lagoons, and compost facilities) that emit unpleasant odors and attract an undesirably large number of birds is provided. The composition of this embodiment includes a bird repelling composition, glycol, and an optional fragrance-containing/odor control composition.

In a variation of the present embodiment, the bird repelling composition is present in an amount from about 0.5 to about 30 weight percent of the total weight of the concentrated treatment composition. In another variation, the bird repelling composition is present in an amount from about 5 to about 28 weight percent of the total weight of the concentrated treatment composition. In still another variation, the bird repelling composition is present in an amount from about 10 to about 25 weight percent of the total weight of the concentrated treatment composition. In yet another variation, the bird repelling composition is present in an amount from about 18 to about 22 weight percent of the total weight of the concentrated treatment composition. Examples of particularly useful bird repelling compositions include methyl anthranilate, dimethyl anthranilate, ethyl anthranilate, diethyl anthranilate, and combinations thereof. Typically, birds experience an unpleasant taste through the eating of grass or other vegetation, drinking of water treated with or the cleaning of feathers that have come into contact with these compositions.

The concentrated treatment composition also includes a glycol. The glycol is used as a diluent and acts to improve the miscibilty of the bird repelling composition with water. In a variation, the glycol is present in an amount from about 70 to 99.5 weight percent of the total weight of the concentrated treatment composition. In another variation, the glycol is present in an amount from about 72 to about 95 weight percent of the total weight of the concentrated treatment composition. In still another variation, the glycol is present in an amount from about 75 to about 90 weight percent of the total weight of the concentrated treatment composition. In yet another variation, the glycol is present in an amount from about 78 to about 82 weight percent of the total weight of the concentrated treatment composition. Examples of useful glycols include, but are not limited to, propylene glycol, ethylene glycol and the like and combinations thereof. Although the present invention is not limited to any particular mode of operation, it appears that the use of glycols as diluents retards the degradation of bird repelling compound(s) (i.e., methyl anthranilate, dimethyl anthranilate, ethyl anthranilate, diethyl anthranilate) by providing protection from solar ultraviolet rays, which are known to rapidly decompose these compounds. The retardation of the decomposition reduces the need for repeated application of the compositions to static surfaces. However, re-application to grasses may be required if grass clippings are collected and removed.

In a variation of the present invention, the concentrated treatment composition also includes a fragrance-containing/odor control composition. In another variation, the fragrance-containing/odor control composition is present in an amount from about 0.001 to 5 weight percent of the total weight of the concentrated treatment composition. In another variation, the fragrance-containing/odor control composition is present in an amount from about 0.01 to about 3 weight percent of the total weight of the concentrated treatment composition. In still another variation, the fragrance-containing/odor control composition is present in an amount from about 0. 1 to about 1 weight percent of the total weight of the concentrated treatment composition. In yet another variation, the fragrance-containing/odor control composition is present in an amount from about 0.1 to about 0.5 weight percent of the total weight of the concentrated treatment composition.

The present invention is further characterized by being substantially free of surfactants. In general, surfactants are not intentionally added to the concentrated composition. In this context, the concentrated composition includes surfactants in an amount less than 0.5 weight percent. Typically, the concentrated composition includes surfactants in an amount less than 0.3 weight percent. In many applications, the concentrated composition includes surfactants in an amount less than 0.1 weight percent.

In another embodiment of the present invention, a diluted treatment composition that is useful for treating environments (e.g., landfills, golf courses, airports, sporting arenas, areas with standing water, waste water treatment plants, athletic fields, retention ponds, lagoons, and compost facilities) that emit unpleasant odors and/or attract an undesirable large number of birds is provided. The composition of this embodiment includes, a bird repelling composition, a glycol, and an optional fragrance-containing/odor control composition. Typically, these diluted compositions correspond to dilutions of the concentrated compositions set forth above. Typically, these dilutions are a factor of 100 to 500. The diluent is typically water.

In a variation of the present embodiment, the bird repelling composition is present in an amount from about 0.001 to about 0.30 weight percent of the total weight of the diluted treatment composition. In another variation, the bird repelling composition is present in an amount from about 0.01 to about 0.28 weight percent of the total weight of the diluted treatment composition. In still another variation, the bird repelling composition is present in an amount from about 0.02 to about 0.25 weight percent of the total weight of the diluted treatment composition. In yet another variation, the bird repelling composition is present in an amount from about 0.036 to about 0.22 weight percent of the total weight of the diluted treatment composition. Example of useful bird repelling compositions include methyl anthranilate, dimethyl anthranilate, ethyl anthranilate, diethyl anthranilate, and combinations thereof.

The diluted treatment composition also includes a glycol. In a variation, the glycol is present in an amount from about 0.14 to 0.995 weight percent of the total weight of the diluted treatment composition. In another variation, the glycol is present in an amount from about 0.144 to about 0.95 weight percent of the total weight of the diluted treatment composition. In still another variation, the glycol is present in an amount from about 0.15 to about 0.90 weight percent of the total weight of the diluted treatment composition. In yet another variation, the glycol is present in an amount from about 0.156 to about 0.82 weight percent of the total weight of the diluted treatment composition. Examples of useful glycols include, but are not limited to, propylene glycol, ethylene glycol and the like and combinations thereof.

In a variation of the present invention, the diluted treatment composition also includes a fragrance-containing/odor control composition. In this context, a fragrance-containing/odor control composition is any composition that neutralizes mal odors associated with decay and nitrogen-containing compounds. In one refinement, such fragrance-containing/odor control compositions include diethyl phthalate, zinc ricinoleate and combinations thereof. In a variation, the fragrance-containing/odor control composition is present in an amount from about 0.000002 to 0.05 weight percent of the total weight of the diluted treatment composition. In another variation, the fragrance-containing/odor control composition is present in an amount from about 0.00002 to about 0.03 weight percent of the total weight of the diluted treatment composition. In still another variation, the fragrance-containing/odor control composition is present in an amount from about 0.0002 to about 0.01 weight percent of the total weight of the diluted treatment composition. In yet another variation, the fragrance-containing/odor control composition is present in an amount from about 0.0002 to about 0.005 weight percent of the total weight of the diluted treatment composition.

The present invention is further characterized by being substantially free of surfactants. In general, surfactants are not intentionally added to the diluted composition. In this context, the diluted composition includes surfactants in an amount less than 0.005 weight percent. Typically, the diluted composition includes surfactants in an amount less than 0.003 weight percent. In many applications, the diluted composition includes surfactants in an amount less than 0.00 1 weight percent.

As set forth above, the concentrated and diluted compositions are useful for bird aversion and odor control. The elimination of objectionable mal odors found in locations that are affected by nuisance birds (such as landfills, transfer stations, golf courses, airports, sporting arenas, areas with standing water, waste water treatment plants, athletic fields, retention ponds, lagoons, and compost facilities) is accomplished through the addition of a fragrance/odor control composition. Typically, this fragrance/odor control composition does not mask odor. Instead, these compositions usually change the character of odor molecules with the perception of a pleasant or indistinct odor rather than a mal odor.

In another embodiment of the present invention, a method of applying the concentrated treatment composition set forth above is provided. In this embodiment, the diluted or concentrated compositions are atomized into an air stream which may be created by a fan and dispersed. In a refinement, the concentrated compositions are diluted into water and sprayed onto landfill surfaces, grasses or other surfaces where the birds are known to frequent. In another variation, the concentrated treatment composition is directly injected into the atmosphere via a high pressure-low volume spraying system or a low pressure-low pressure spraying system.

In another embodiment of the present invention, a method of applying the concentrated treatment compositions set forth above is provided. The method of this embodiment includes a step in which the concentrated treatment composition is injected into water under pressure from about 100 psi to about 1500 psi. The resulting composition is then directed through nozzles into the atmosphere or onto the ground or other surfaces.

In another embodiment of the present invention, a method of applying the concentrated treatment compositions set forth above is provided. The method of this embodiment includes a step in which a solution of the concentrated treatment composition and water is created. Typically, the weight ratio of concentrated treatment composition to water is from about 1 to 100 to about 1 to 500. This solution is then applied by various means onto surfaces or into the atmosphere.

The following examples illustrate the various embodiments of the present invention. Those skilled in the art will recognize many variations that are within the spirit of the present invention and scope of the claims.

Tables 1-4 provide examples of concentrated treatment compositions that are useful for bird repelling application.

TABLE 1

Treatment composition

| component | Weight Percent |
|---|---|
| Methyl anthranilate | 19.5 |
| fragrance-containing/odor control | 0.5 |
| propylene glycol | 79.5 |

TABLE 2

Treatment composition

| component | Weight Percent |
|---|---|
| Methyl anthranilate | 22 |
| fragrance-containing/odor control | 0.5 |
| propylene glycol | 77.5 |

TABLE 3

Treatment composition

| component | Weight Percent |
|---|---|
| Methyl anthranilate | 16 |
| fragrance-containing/odor control | 1.6 |
| propylene glycol | 82.4 |

TABLE 4

Treatment composition

| component | Weight Percent |
|---|---|
| Methyl anthranilate | 20 |
| fragrance-containing/odor control | 2 |
| propylene glycol | 78 |

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A concentrated treatment composition for odor and bird control consisting of:
    a bird repelling composition present in an amount from about 18 to about 22 weight percent of the total weight of the concentrated treatment composition, wherein the bird repelling composition is selected from the group consisting of methyl anthranilate, dimethyl anthranilate, ethyl anthranilate, diethyl anthranilate, and combinations thereof;
    a fragrance-containing/odor control composition present in an amount from about 0.1 to about 1 weight percent of the total weight of the concentrated treatment composition; and
    a glycol present in an amount from about 78 to about 82 weight percent of the total weight of the concentrated treatment composition.

2. The concentrated treatment composition of claim 1 wherein the glycol is a component selected from the group consisting of propylene glycol, ethylene glycol and combinations thereof.

* * * * *